United States Patent [19]

Dubief et al.

[11] Patent Number: 5,804,207
[45] Date of Patent: Sep. 8, 1998

[54] DETERGENT COSMETIC COMPOSITIONS CONTAINING A THICKENING POLYACRYLAMIDE

[75] Inventors: Claude Dubief, Le Chesnay; Danièle Cauwet-Martin, Paris, both of France

[73] Assignee: L'Oreal, Paris, France

[21] Appl. No.: 816,800

[22] Filed: Mar. 19, 1997

[30] Foreign Application Priority Data

Mar. 21, 1996 [FR] France .................................. 96 03542
Feb. 7, 1997 [EP] European Pat. Off. .............. 97400283

[51] Int. Cl.$^6$ .............................. A61K 6/00; A61K 7/00; A61K 7/06
[52] U.S. Cl. ........................................... 424/401; 424/70.1
[58] Field of Search .................................. 424/401, 70.1, 424/70.4, 70.19, 70.22, 70.24, 70.31, 70.21, 70.12, 70.13; 514/828, 844, 877, 880, 881

[56] References Cited

U.S. PATENT DOCUMENTS

| | | | |
|---|---|---|---|
| 4,213,980 | 7/1980 | Grollier et al. | 424/47 |
| 5,294,693 | 3/1994 | Egraz et al. | 526/310 |
| 5,324,765 | 6/1994 | Mondet et al. | 524/423 |
| 5,362,415 | 11/1994 | Egraz et al. | 252/174.24 |
| 5,556,628 | 9/1996 | Derian et al. | 424/401 |

FOREIGN PATENT DOCUMENTS

| | | |
|---|---|---|
| A-0231997 | 8/1987 | European Pat. Off. . |
| A-0494022 | 7/1992 | European Pat. Off. . |
| A-0577526 | 1/1994 | European Pat. Off. . |
| A-2694494 | 2/1994 | France . |
| A-9427574 | 12/1994 | WIPO . |

Primary Examiner—Thurman K. Page
Assistant Examiner—Sharon Howard
Attorney, Agent, or Firm—Finnegan, Henderson, Farabow, Garrett & Dunner, L.L.P.

[57] ABSTRACT

A cosmetic composition intended for cleaning the hair, the scalp and/or the skin, containing detergent surfactants, co-surfactants, at least one electrolyte and at least one thickening polyacrylamide, and their use in cosmetic applications.

36 Claims, No Drawings

DETERGENT COSMETIC COMPOSITIONS CONTAINING A THICKENING POLYACRYLAMIDE

The present invention relates to novel cosmetic compositions intended for cleaning the hair, the scalp and/or the skin, containing at least one detergent anionic) surfactant, at least one co-surfactant, at least one electrolyte and at least one thickening polyacrylamide, as well as to their use in cosmetic applications.

It is common to use detergent cosmetic compositions, i.e., shampoos or shower gels, containing surfactants with washing power and one or more conditioners to clean the hair and/or the skin.

Indeed, in order to improve the cosmetic properties of detergent compositions, and more particularly detergent compositions to be applied to sensitized hair, i.e., hair which has been damaged or made brittle, in particular under the chemical action of atmospheric agents and/or hair treatments, such as permanent waving, dyeing or bleaching, it is often necessary to introduce into the compositions cosmetic conditioners such as, for example, silicones, which make the treated hair easy to disentangle and to style, as well as affording markedly enhanced softness and sheen.

Similarly, it may be advantageous to treat the scalp with compositions containing active agents such as antidandruff agents.

Because of the insoluble nature of most of the conditioners or certain antidandruff agents in the aqueous media used in shampoos, these agents are maintained in dispersed form. This dispersed form allows conditioners or antidandruff agents to be deposited on the hair or on the skin and not to be totally removed during rinsing. It is important, however, that the suspension of these agents does not disrupt the detergent and foaming properties of the cosmetic composition.

Few means exist at the present time for keeping insoluble agents in suspension efficiently. To this end, the use of long-chain ester or ether derivatives or polysaccharides such as xanthan gum have already been proposed. However, long-chain esters or ethers have crystallization problems which lead to a change, i.e., increase in the viscosity of the compositions over time. Gelling polysaccharides also have drawbacks, namely, that it is difficult to make detergent compositions containing them foam, i.e., poor initiation of foaming and the compositions do not have a smooth texture and flow in blobs, which is not appreciated by users.

French Patent Application No. 2,694,494 proposes compositions containing, in suspension, water-insoluble particles containing an anionic surfactant, a nonionic or amphoteric co-surfactant and an electrolyte, the surfactants being present in an amount such that the composition has a pseudo plastic behavior with a flow threshold greater than 0.2 Pa and has a lamellar phase structure including spherulites capable of maintaining water-insoluble particles in suspension.

However, these compositions, which allow particles to be placed in suspension, are unsatisfactory, in particular when they are used as shampoos or shower gels. In particular, the foaming properties, such as the initiation of foaming, are not entirely satisfactory. The foams are generally too compact and difficult to work.

Applicants have thus sought to improve the foaming properties of these compositions, while at the same time retaining good properties of use such as the appearance and the handling of the composition. The reason for this is that it is preferable to have compositions having a viscosity which is sufficient for them to be taken easily from the container.

An object of the present invention is thus detergent cosmetic compositions possessing good foaming properties, which are capable of maintaining water-insoluble conditioners in suspension and which are of sufficient viscosity.

Applicants have found that these objectives are achieved by introducing a thickening polyacrylamide into a medium comprising at least one anionic surfactant, at least one nonionic or amphoteric co-surfactant and at least one electrolyte, the anionic surfactant and the nonionic or amphoteric surfactant bieng present in a co-surfactant/anionic surfactant weight ratio of less than or equal to 1, wherein the compounds are present in an amount effective to provide the composition with the following characteristics:
(a) a rheological flow behavior characterized by a stress range for which the viscosity is constant, followed by a stress range for which the viscosity decreases as the stress increases, and
(b) a lamellar phase structure capable of maintaining in suspension water-insoluble particles which may be present in the composition.

The foaming properties of the compositions, such as the initiation of foaming, are markedly improved and the compositions are of sufficient viscosity. The compositions according to the invention are stable; they allow water-insoluble particles to be maintained in suspension.

A subject of the invention is thus a detergent cosmetic composition comprising:
(a) at least one anionic surfactant;
(b) at least one nonionic or amphoteric co-surfactant;
(c) at least one thickening polyacrylamide; and
(d) at least one electrolyte;
wherein the at least one nonionic or amphoteric co-surfactant and the at least one anionic surfactant are present in a co-surfactant/anionic surfactant weight ratio of less than or equal to 1; and further wherein the at least one anionic surfactant, the at least one nonionic or amphoteric co-surfactant, the at least one thickening polyacrylamide and the at least one electrolyte are each present in an amount effective to provide the composition with:
(i) a rheological flow behavior having a stress range for which the viscosity is constant, followed by a stress range for which the viscosity decreases as the stress increases, and
(ii) a lamellar phase structure capable of maintaining in suspension water-insoluble particles which may be present in the composition.

Furthermore, the compositions of the invention have advantageous washing properties and cosmetic properties i.e., softness, disentangling, and styling. Lastly, the compositions have a non-runny and melting texture.

Another subject of the invention is a cosmetic process for cleaning the hair, the skin and/or the scalp using the above described compositions.

The rheological flow behavior of the compositions is characterized using an imposed-stress rheometer (Carrimed CSHR100). The measurements are taken at 25° C. using a plate-and-cone measuring device with a cone angle of 2 degrees and a diameter of 6 cm.

The stresses, for which the viscosity of a given composition is constant, are variable. Preferably, according to the present invention, they range from 0.001 to 10 Pa, and more preferably from 0.01 to 2 Pa.

The compositions according to the invention have a lamellar phase, i.e., a hydrated solid phase or a liquid crystal phase in which several bilayers are arranged in a parallel network, separated by layers of water or of aqueous solution.

The lamellar phase may optionally contain spherulites which are multi lamellar vesicles containing several layers of surfactants arranged concentrically and ranging from 0.1 to 50 micrometers in size.

As examples of anionic surfactants which are preferably used, alone or as mixtures, in the context of the present invention, mention may be made in particular of salts, such as, alkali metal salts, especially sodium salts, ammonium salts, amine salts, amino alcohol salts or magnesium salts of the following compounds: alkyl sulphates, alkyl ether sulphates, alkylamidoether sulphates, monoglyceride sulphates, alkylglyceryl sulphonates, alkyl sulphonates, alkyl phosphates, alkyl amide sulphonates, alkylaryl sulphonates, α-olefin sulphonates, alkyl sulphosuccinates, alkyl ether sulphosuccinates, alkyl amide sulphosuccinates, alkyl sulphosuccinamates, alkyl sulphoacetates, alkyl ether phosphates, acyl isethionates and N-acylamino acids such as N-acylsarcosinates, N-acylglutamates and N-acyltaurates. Mention may also preferably be made of fatty acid salts, such as the salts of undecylenic, oleic, ricinoleic, palmitic and stearic acids, coconut oil acid and hydrogenated coconut oil acid, and acylhydroxy acids such as acyllactylates. Weakly anionic surfactants may also be used, such as alkyl-D-galactosiduronic acids and salts thereof, as well as polyoxyalkylenated carboxylic acid ethers, in particular those containing from 2 to 24 ethylene oxide groups, and mixtures thereof. The alkyl or acyl radical of all of these different compounds preferably contains from 8 to 22 carbon atoms.

By way of nonionic co-surfactants which are preferably used according to the invention, mention may be made of ethoxylated, propoxylated or glycerolated fatty acids, alkylphenols, alpha-diols or alcohols, each having a fatty chain containing from 8 to 28 carbon atoms, it being possible for the number of ethylene oxide or propylene oxide groups to range from 1 to 50 and the number of glycerol groups to range in particular from 1 to 30. Mention may also be made of copolymers of ethylene oxide and propylene oxide, condensates of ethylene oxide and propylene oxide with fatty alcohols, polyethoxylated fatty amines or amides preferably having from 2 to 30 mol of ethylene oxide, polyglycerolated fatty amides containing on average from 1 to 5 glycerol groups, polyglycerolated diglycolamides, optionally oxyethylenated fatty acid esters of sorbitan, fatty acid esters of sucrose, polyoxyalkylenated fatty acid esters, optionally oxyalkylenated alkylpolyglycosides, alkylglucoside esters, N-alkylglucamine and N-acylmethylglucamine derivatives, amine oxides and mixtures thereof.

By way of amphoteric co-surfactants which are preferably used according to the invention, mention may be made of secondary or tertiary aliphatic amine derivatives in which the aliphatic radical is a linear or branched chain containing from 8 to 22 carbon atoms and containing at least one water-solubilizing anionic group for example, carboxylate, sulphonate, sulphate, phosphate or phosphonate; mention may also be made of alkylbetaines, alkyldimethylbetaines, alkylsulphobetaines, alkylamidobetaines, alkylamidoalkylsulphobetaines, imidazoline derivatives such as amphocarboxyglycinate or amphocarboxypropionate derivatives, and mixtures thereof. Mixtures of co-surfactants may also be used.

The more preferred co-surfactants according to the invention are selected from ethoxylated fatty alcohols and betaine derivatives.

The anionic surfactant(s) are preferably present in the compositions according to the invention in amounts ranging from 3 to 50% by weight, and more preferably from 5 to 30% by weight, relative to the total weight of the composition.

The co-surfactant(s) are preferably present in the compositions according to the invention in amounts ranging from 0.05 to 20% by weight, and more preferably from 1 to 15% by weight, relative to the total weight of the composition.

The sum of the concentrations of anionic surfactants and co-surfactants preferably ranges from 3 to 70% by weight relative to the total weight of the composition.

The co-surfactant/anionic surfactant weight ratio preferably ranges from 0.01 to 1 and more preferably ranges from 0.05 to 0.75.

According to the invention, any type of electrolyte which is known per se can be used. It is preferred to use electrolytes whose solubility in water ranges from 0.1 g % to 300 g % by weight relative to the total weight of the composition and even more preferably from 10 to 50 g %.

Among the electrolytes, mention may particularly be made of metal salts, amine salts, ammonium salts and basic amino acid salts.

The metal salts are preferably selected from salts of alkali metals, of alkaline-earth metals, of transition metals and of metals of groups IIIA and IVA of the Periodic Table of the Elements.

As alkali metal salts which are useful according to the invention, mention may be made in particular of the lithium, sodium and potassium salts.

As alkaline-earth metal salts which are useful according to the invention, mention may be made in particular of the beryllium, magnesium, calcium, strontium and/or barium salts.

As transition metal salts which are useful according to the invention, mention may be made in particular of the lanthanide salts and the salts of metals of the fourth period of the Periodic Table of the Elements, such as the manganese, cobalt and zinc salts.

As salts of metals of groups IIIA and IVA of the Periodic Table of the Elements which are useful according to the invention, mention may be made of the aluminium and tin salts.

In the context of the present invention, the term "lanthanide" is understood to refer to elements of atomic number ranging from 57 to 71, i.e., lanthanum, cerium, praseodymium, neodymium, promethium, samarium, europium, gadolinium, terbium, dysprosium, holmium, erbium, thulium, ytterbium and lutetium.

The metal salts according to the invention are preferably selected from the lithium, strontium, barium, yttrium, neodymium, gadolinium, manganese and zinc salts, and even more preferably from strontium salts.

These salts may be, for example, carbonates, bicarbonates, sulphates, glycerophosphates, borates, chlorides, nitrates, acetates, hydroxides or persulphates, as well as salts of a-hydroxy acids or salts of fruit acids, such as citrate, tartrate, lactate, malate or alternatively salts of amino acids such as aspartate, arginate, glucocholate, fumarate, or salts of fatty acids, such as palmitate, oleate, caseinate, and behenate.

The salt is preferably selected from nitrates or chlorides, in particular lithium, strontium, barium, yttrium, neodymium, gadolinium, manganese and zinc nitrate, lithium, strontium, barium, yttrium, neodymium, gadolinium, manganese and zinc chloride, and sulphates and acetates, such as calcium, strontium and magnesium sulphate and strontium and magnesium acetate.

Even more advantageously, the electrolyte is a magnesium or strontium salt, in particular one in the form of the chloride or nitrate.

According to the invention, the electrolyte concentration is preferably less than 20% by weight relative to the total weight of the composition and more preferably ranges from 2 to 15%.

The thickening polyacrylamides according to the invention are preferably polyacrylamides whose solution in water at a concentration of 0.1% by weight has a viscosity of greater than about 5 mPa.s measured at 25° C. with a Contraves TV module 1 viscometer.

The thickening polyacrylamides may preferably be selected from:

optionally crosslinked copolymers of acrylamide and ammonium acrylate;

optionally crosslinked copolymers of acrylamide or methacrylamide and methacryloyloxyethyltrimethylammonium halide, for example chloride; and optionally crosslinked and partially or totally neutralized copolymers of acrylamide and 2-acrylamido-2-methylpropanesulphonic acid.

The crosslinked acrylamide/ammonium acrylate copolymer used in accordance with the present invention is preferably an acrylamide/ammonium acrylate copolymer (5/95 by weight) crosslinked with a cross linking agent containing olefinic polyunsaturation, such as divinylbenzene, tetraallyloxyethane, methylenebisacrylamide, diallyl ether, polyallylpolyglyceryl ethers or allylic ethers of alcohols of the sugar series, such as erythritol, pentaerythritol, arabitol, mannitol, sorbitol and glucose.

Similar copolymers are described and prepared in French Patent No. FR 2,416,723 and U.S. Pat. Nos. 2,798,053 and 2,923,692, the disclosures of which are incorporated herein by reference.

Preferably, this crosslinked copolymer is used in the form of a water-in-oil emulsion containing about 30% by weight of the copolymer, about 25% by weight of liquid paraffin, about 4% by weight of a mixture of sorbitan stearate and a hydrophilic ethoxylated derivative and about 41% by weight of water. Such an emulsion is marketed under the name BOZEPOL C by the company Hoechst.

The copolymers of acrylamide and 2-acrylamido-2-methylpropanesulphonic acid which are used in accordance with the present invention are copolymers crosslinked with a compound containing olefinic polyunsaturation, such as those mentioned above, and partially or totally neutralized with a neutralizing agent such as sodium hydroxide, potassium hydroxide, aqueous ammonia or an amine such as triethanolamine or monoethanolamine. They may be prepared by copolymerizing acrylamide and sodium 2-acrylamido-2-methylpropanesulphonate via a radical route using initiators of the azobisisobutyronitrile type and by precipitation from an alcohol such as tert-butanol.

Copolymers obtained by copolymerization of from 70 to 55 mol % of acrylamide and from 30 to 45 mol % of sodium 2-acrylamido-2-methylpropane-sulphonate are even more preferably used. The crosslinking agent is used at concentrations preferably ranging from $10^{-4}$ to $4 \times 10^4$ mol per mole of the mixture of monomers.

These specific copolymers are incorporated into the compositions of the invention, preferably, in the form of water-in-oil emulsions containing from 35 to 40% by weight of this copolymer, from 15 to 25% by weight of a mixture of $C_{12}$–$C_{13}$ isoparaffin hydrocarbons, from 3 to 8% by weight of polyethylene glycol lauryl ether containing 7 mol of ethylene oxide, and water. Such an emulsion is marketed under the name SEPIGEL 305 by the company Seppic.

The crosslinked copolymer of acrylamide and methacryloyloxyethyltrimethyl-ammonium chloride used according to the invention is more preferably a copolymer obtained by copolymerization of acrylamide and dimethylaminoethyl methacrylate quaternized with methyl chloride, followed by crosslinking with a compound containing olefinic unsaturation, in particular methylenebisacrylamide.

A crosslinked acrylamide/methacryloyloxyethyltrimethylammonium chloride copolymer (about 50/50 by weight) in the form of a dispersion containing 50% by weight of the said copolymer in mineral oil is even more preferably used. This dispersion is marketed under the name SALCARE SC92 by the company Allied Colloids.

The non-crosslinked copolymers of methacrylamide and methacryloyloxy-ethyltrimethylammonium chloride are, for example, the products sold under the brand names ROHAGIT KF 400 and KF720 by the company Rohm.

The thickening polyacrylamides are preferably present in the compositions according to the invention in amounts ranging from 0.05 to 5% by weight, and more preferably from 0.2 to 3% by weight, relative to the total weight of the composition.

The compositions according to the invention preferably have a viscosity greater than 300 mPa.s.

In the context of the present invention the term "water-insoluble particles" is understood to denote solid or non-solid species which do not dissolve in the aqueous medium of the composition.

The water-insoluble particles which may be dispersed in the compositions according to the invention are, for example, modified or unmodified silicone oils, resins or gums, fluoro compounds, antidandruff agents, plant, mineral or synthetic oils, waxes, pearlescent agents, pigments, fatty acid esters, abrasive particles such as silica, fragrances and polymers which are insoluble in water.

The detergent compositions according to the invention have a final pH preferably ranging from 3 to 8. More preferably, the pH ranges from 4 to 7.5. The pH can be adjusted to the desired value by the conventional addition, depending on the case, of either basifying agents or of acidifying agents, which are common and known to be cosmetically acceptable.

The detergent compositions according to the invention may, of course, also contain all the adjuvants usually encountered in the field of detergent compositions for the hair and/or the body, such as, for example, fragrances, preserving agents, sequestering agents, acidifying agents, basifying agents, softeners, foam modifiers, dyes, pearlescent agents, moisturizers, antidandruff agents or antiseborrhoeic agents, vitamins, silicones, ceramides, sun screens, polymers, preferably cationic or amphoteric polymers, and the like.

Obviously, a person skilled in the art will select the optional compound or compounds to be added to the composition according to the invention such that the advantageous properties intrinsically associated with the composition in accordance with the invention are not, or are substantially not, adversely affected by the addition envisaged.

These compositions may be in the form of thickened liquids, creams or gels and they are mainly suitable for washing the hair and/or the skin.

Another subject of the invention is a process for washing the skin or keratin fibres, such as the hair, which comprises applying to the skin or keratin fibres a composition as defined above, followed by rinsing with water.

Concrete examples illustrating the invention will now be given.

In the following text, "AM" means active material.

EXAMPLE 1

A shampoo in accordance with the invention, which had the following composition, was prepared:

| | | |
|---|---|---|
| Sodium lauryl ether sulphate containing 2.2 mol of ethylene oxide, as an aqueous solution containing 28% AM | | 11.2 g AM |
| Oleylamidopropyldimethylbetaine as an aqueous solution containing 28% AM | | 8.4 g AM |
| Selenium disulphide | | 0.5 g |
| NaCl | | 3 g |
| Polyacrylamide as a reverse emulsion containing 40% AM (SEPIGEL 305 from Seppic) | | 1 g AM |
| Preserving agents, dyes, fragrance | qs | |
| HCl | qs | pH 6.5 |
| Water qs | | 100 g |

This shampoo was in the form of a thick milk. It was applied to wet hair and a pleasant, creamy foam was rapidly obtained. It had good foaming properties, made the hair feel soft and made it easy to disentangle.

The composition had a flow profile with a stress range for which the viscosity was constant, followed by a stress range for which the viscosity decreased as the stress increased. Observation of the composition under an optical or electronic microscope indicated a lamellar structure.

The composition was stable and the selenium disulphide was maintained in suspension.

EXAMPLE 2

A shampoo in accordance with the invention, which had the following composition, was prepared:

| | | |
|---|---|---|
| Sodium lauryl ether sulphate containing 2.2 mol of ethylene oxide, as an aqueous solution containing 28% AM | | 21 g AM |
| Polyoxypropylenated ($C_{12}$–$C_{15}$) alcohol containing 3 mol of propylene oxide | | 3 g |
| Polydimethylsiloxane (PDMS) (oil 47 V 500,000 Rhône-Poulenc) | | 3 g |
| NaCl | | 10 g |
| Polyquaternium-32 (CTFA) as a reverse emulsion containing 50% AM (SALCARE SC 92 from Allied Colloid) | | 0.5 g AM |
| Preserving agents, dyes, fragrance | qs | |
| NaOH | qs | pH 6.8 |
| Water | qs | 100 g |

This shampoo was in the form of a creamy milk. It had good foaming properties, made the hair feel soft and made the hair easy to disentangle.

The composition had a flow profile with a stress range for which the viscosity was constant, followed by a stress range for which the viscosity decreased as the stress increased. Observation of the composition under an optical or electronic microscope indicated a lamellar structure.

The composition was stable and the silicone was maintained in suspension.

EXAMPLE 3 (Invention)

A shampoo in accordance with the invention, which had the following composition, was prepared:

| | | |
|---|---|---|
| Sodium lauryl ether sulphate containing 2.2 mol of ethylene oxide, as an aqueous solution containing 28% AM | | 16.6 g AM |
| Oleylamidopropyldimethylbetaine as an aqueous solution containing 28% AM | | 2.7 g AM |
| Polydimethylsiloxane (PDMS) (oil 47 V 560,000 Rhône-Poulenc) | | 2.7 g |
| Dimethicone copolyol sold under the name DC 190 by the company Dow Corning | | 1 g |
| NaCl | | 12 g |
| Polyacrylamide as a reverse emulsion containing 40% AM (SEPIGEL 305 from Seppic) | | 1 g AM |
| Preserving agents, dyes, fragrance | qs | |
| HCl | qs | pH 6.5 |
| Water | qs | 100 g |

This shampoo was in the form of a creamy milk. It had good foaming properties, made the hair feel soft and made the hair easy to disentangle.

The composition had a flow profile with a stress range for which the viscosity was constant, followed by a stress range for which the viscosity decreased as the stress increased. Observation of the composition under an optical or electronic microscope indicated a lamellar structure. The composition had a viscosity of about 1500 mPa.s (measured at 25° C. with a Contraves TV module 3 viscometer).

The composition was stable and the silicones were maintained in suspension.

EXAMPLES 4.5.6 and 7 (COMPARATIVE)

Shampoos similar to that of Example 3, in which the polyacrylamide was replaced with the same amount of another thickener, were prepared:

Example 4: xanthan gum
Example 5: crosslinked acrylic copolymer (CARBOPOL 1342 from Goodrich)
Example 6: hydroxyethylcellulose (NATROSOL 250 HHR from National Starch)
Example 7: crosslinked copolymer of methyl vinyl ether and maleic anhydride (STABILEZE 06 from ISP)

The foaming power of these compositions was evaluated by a panel of testers experienced in evaluating the criteria of development and abundance of foam.

1.5 g of each composition was applied to locks of 5 g of hair moistened with water and dried by passing through the fingers. The tester massaged each lock with clean and wet hands in order to develop the foam.

Composition 3 according to the invention had an excellent foaming power. Compositions 4, 5, 6 and 7 had a foaming power which was very much inferior to that of composition 3. The foam developed more slowly and the foam obtained was less abundant.

Only the composition of Example 3, according to the invention, had a satisfactory foaming power.

Moreover, compositions 4, 5, 6 and 7 were unstable. After storage for one month at 45° C., phase separation took place and the silicone was released at the surface; the silicone was not maintained in suspension.

What is claimed is:

1. A detergent cosmetic composition comprising:
   (a) at least one anionic surfactant;
   (b) at least one nonionic or amphoteric co-surfactant;
   (c) at least one thickening polyacrylamide; and
   (d) at least one electrolyte;
   wherein said at least one nonionic or amphoteric co-surfactant and said at least one anionic surfactant are present in a co-surfactant/anonic surfactant weight ratio of less than or equal to 1; and further wherein said at least one anionic surfactant, said at least one nonionic or amphoteric co-surfactant, said at least one thickening polyacrylamide and said at least one electrolyte are each present in an amount effective to provide said composition with:
   (i) a rheological flow behavior having a stress range for which the viscosity is constant, followed by a stress range for which the viscosity decreases as the stress increases, and
   (ii) a lamellar phase structure capable of maintaining in suspension water-insoluble particles which may be present in said composition.

2. A composition according to claim 1, wherein said at least one anionic surfactant is an alkyl sulphate, alkyl ether sulphate, alkylamidoether sulphate, monoglyceride sulphate, alkylglyceryl sulphonate, alkyl sulphonate, alkyl phosphate, alkylamide sulphonate, alkylaryl sulphonate, a-olefin sulphonate, alkyl sulphosuccinate, alkyl ether sulphosuccinate, alkylamide sulphosuccinate, alkyl sulphosuccinamate, alkyl sulphoacetate, alkyl ether phosphate, acyl isethionate, an N-acylamino acid, a fatty acid salt, an alkyl-D-galactosiduronic acid or salt thereof, a polyoxyalkylenated carboxylic acid ether, or a mixture of any of the above.

3. A composition according to claim 2, wherein said N-acylamino acid is an N-acylsarcosinate, N-acylglutamate or N-acyltaurate.

4. A composition according to claim 2, wherein said fatty acid salt is a salt of undecylenic acid, oleic acid, ricinoleic acid, palmitic acid, stearic acid, coconut oil acid, hydrogenated coconut oil acid or acylhydroxy acid.

5. A composition according to claim 4, wherein said acylhydroxy acid is an acyl lactylate.

6. A composition according to claim 2, wherein said polyoxyalkylenated carboxylic acid ether contains from 2 to 24 ethylene oxide groups.

7. A composition according to claim 1, wherein said nonionic co-surfactant is an ethoxylated, propoxylated or glycerolated fatty acid; an alkylphenol; an alpha-diol or alcohol, each having a fatty chain containing from 8 to 28 carbon atoms; a copolymer of ethylene oxide and propylene oxide; a condensate of ethylene oxide and propylene oxide with a fatty alcohol; a polyethoxylated fatty amine; a polyethoxalated fatty amide; a polyglycerolated fatty amide containing from 1 to 5 glycerol groups; a polyglycerolated diglycolamide; an optionally oxyethylenated fatty acid ester of sorbitan; a fatty acid ester of sucrose; a polyoxyalkylenated fatty acid ester; an optionally oxyalkylenated alkylpolyglycoside; an alkylglucoside ester; an N-alkylglucamine or N-acylmethylglucamine derivative; an amine oxide or a mixture of any of the above.

8. A composition according to claim 7, wherein the number of ethylene oxide or propylene oxide groups in said ethoxylated or propoxylated fatty acid, alkylphenol, alpha-diol or alcohol ranges from 1 to 50.

9. A composition according to claim 7, wherein the number of glycerol groups in said glycerated fatty acid, alkylphenol, alpha-diol or alcohol ranges from 1 to 30.

10. A composition according to claim 7, wherein said polyethoxylated fatty amine and said polyethoxylated fatty amide contain from 2 to 30 moles of ethylene oxide.

11. A composition according to claim 1, wherein said at least one amphoteric co-surfactant is a secondary or tertiary aliphatic amine derivative in which the aliphatic radical is a linear or branched chain containing from 8 to 22 carbon atoms and containing at least one anionic water-solubilizing carboxylate, sulphonate, sulphate, phosphate or phosphonate group.

12. A composition according to claim 11, wherein said at least one amphoteric co-surfactant is an alkylbetaine, alkyldimethylbetaine, alkylsulphobetaine, alkylamidoalkylbetaine, alkylamidoalkylsulphobetaine, imidazoline derivative or amphocarboxypropionate derivative, or a mixture thereof.

13. A composition according to claim 12, wherein said imidazoline derivative is an amphocarboxyglycinate.

14. A composition according to claim 1, wherein said at least one anionic surfactant is present in an amount ranging from 3 to 50% by weight relative to the total weight of the composition.

15. A composition according to claim 14, wherein said at least one anionic surfactant is present in an amount ranging from 5 to 30% by weight relative to the total weight of the composition.

16. A composition according to claim 1, wherein said at least one co-surfactant is present in an amount ranging from 0.05 to 20% by weight relative to the total weight of the composition.

17. A composition according to claim 16, wherein said at least one co-surfactant is present in an amount ranging from 1 to 10% by weight relative to the total weight of the composition.

18. A composition according to claim 1, wherein said at least one electrolyte is present in an amount of less than 20% by weight relative to the total weight of the composition.

19. A composition according to claim 18, wherein said at least one electrolyte is present in an amount ranging from 2 to 15% by weight relative to the total weight of the composition.

20. A composition according to claim 1, wherein said at least one electrolyte has a solubility in water ranging from 0.1 to 300 g %.

21. A composition according to claim 20, wherein said at least one electrolyte has a solubility in water ranging from 10 to 50 g %.

22. A composition according to claim 1, wherein said at least one electrolyte is a metal salt, an amine salt, an ammonium salt or a basic amino acid salt.

23. A composition according to claim 22, wherein said metal salt is a salt of an alkali metal, of an alkaline-earth metal, of a transition metal or of a metal from groups IIIA or IVA of the Periodic Table of the Elements.

24. A composition according to claim 23, wherein said metal salt is a lithium, magnesium, strontium, barium, yttrium, neodymium, gadolinium, manganese or zinc salt.

25. A composition according to claim 24, wherein said salt is a magnesium or strontium salt.

26. A composition according to claim 22, wherein said metal salt is a carbonate, bicarbonate, sulphate, glycerophosphate, borate, chloride, nitrate, acetate, hydroxide or persulphate, a salt of an a-hydroxy acid, an amino acid salt or a fatty acid salt.

27. A composition according to claim 26, wherein said salt is strontium chloride or nitrate.

28. A composition according to claim 1, wherein said at least one thickening polyacrylamide is:

an optionally crosslinked copolymer of acrylamide and ammonium acrylate;

an optionally crosslinked copolymer of acrylamide and methacryloyloxyethyltri-methylammonium chloride; or an optionally crosslinked and partially or totally neutralized copolymer of acrylamide and 2-acrylamido-2-methylpropanesulphonic acid.

29. A composition according to claim 1, wherein said at least one thickening polyacrylamide is present in an amount ranging from 0.05 to 5% by weight relative to the total weight of the composition.

30. A composition according to claim 29, wherein said at least one thickening polyacrylamide is present in an amount ranging from 0.2 to 3% by weight relative to the total weight of the composition.

31. A composition according to claim 1, wherein said co-surfactant/anionic surfactant weight ratio ranges from 0.01 to 1.

32. A composition according to claim 31, wherein said co-surfactant/anionic surfactant weight ratio ranges from 0.05 to 0.75.

33. A process for cleaning the skin or keratin fibres, said process comprising the step of applying an effective amount of at least one detergent cosmetic composition according to claim 1 to said skin or keratin fibres and then rinsing said keratin fibre.

34. A process according to claim 33, wherein said keratin fibre is hair.

35. A process for washing the skin or keratin fibres, said process comprising the step of applying an effective amount of at least one detergent cosmetic composition according to claim 1 to said skin or keratin fibres and then rinsing said keratin fibre.

36. A process according to claim 35, wherein said keratin fibre is hair.

* * * * *

UNITED STATES PATENT AND TRADEMARK OFFICE
CERTIFICATE OF CORRECTION

PATENT NO. : 5,804,207
DATED : September 8, 1998
INVENTOR(S) : Claude Dubief, et. al.

It is certified that error appears in the above-identified patent and that said Letters Patent is hereby corrected as shown below:

In claim 2, col. 9, line 28, change "a-olefin" to --α-olefin--.

In claim 26, col. 10, line 62, change "a-hydroxy to -- α-hydroxy --.

Signed and Sealed this

Twelfth Day of January, 1999

*Attest:*

*Attesting Officer*   *Acting Commissioner of Patents and Trademarks*